United States Patent
Frommer et al.

(10) Patent No.: US 8,173,863 B2
(45) Date of Patent: May 8, 2012

(54) SUCROSE BIOSENSORS AND METHODS OF USING THE SAME

(75) Inventors: Wolf B. Frommer, Stanford, CA (US); Ida Lager, Lund (SE)

(73) Assignee: Carnegie Institution of Washington, Washington, DC (US)

( * ) Notice: Subject to any disclaimer, the term of this patent is extended or adjusted under 35 U.S.C. 154(b) by 650 days.

(21) Appl. No.: 12/083,196

(22) PCT Filed: Oct. 14, 2005

(86) PCT No.: PCT/US2005/036951
§ 371 (c)(1),
(2), (4) Date: Feb. 27, 2009

(87) PCT Pub. No.: WO2007/046786
PCT Pub. Date: Apr. 26, 2007

(65) Prior Publication Data
US 2009/0188001 A1 Jul. 23, 2009

(51) Int. Cl.
*C12N 15/82* (2006.01)
*C12N 15/81* (2006.01)
*G01N 33/53* (2006.01)
*C07H 21/04* (2006.01)
*C07K 14/00* (2006.01)

(52) U.S. Cl. ...... 800/278; 435/7.1; 435/320.1; 435/483; 536/23.4; 530/350

(58) Field of Classification Search .................. 800/234
See application file for complete search history.

(56) References Cited

U.S. PATENT DOCUMENTS

| | | | |
|---|---|---|---|
| 5,795,729 A | 8/1998 | Lee | |
| 5,981,200 A | 11/1999 | Tsien | |
| 5,998,204 A | 12/1999 | Tsien | |
| 6,197,534 B1 | 3/2001 | Lakowicz | |
| 6,277,627 B1 | 8/2001 | Hellinga | |
| 6,376,257 B1 | 4/2002 | Persechini | |
| 6,465,199 B1 | 10/2002 | Craig | |
| 6,469,154 B1 | 10/2002 | Tsien | |
| 2002/0058273 A1 | 5/2002 | Shipwash | |
| 2003/0061634 A1* | 3/2003 | Grimes et al. | 800/284 |
| 2003/0134346 A1 | 7/2003 | Amiss | |
| 2004/0029129 A1 | 2/2004 | Wang | |
| 2004/0118681 A1 | 6/2004 | Hellinga | |
| 2005/0112685 A1 | 5/2005 | Amiss | |
| 2005/0196768 A1 | 9/2005 | Campbell | |
| 2010/0037329 A1* | 2/2010 | Frommer et al. | 800/13 |

FOREIGN PATENT DOCUMENTS

| | | |
|---|---|---|
| WO | WO 00/49183 | 8/2000 |
| WO | WO 01/18237 | 3/2001 |
| WO | WO 03/025220 | 3/2003 |

OTHER PUBLICATIONS

Fehr et al, Visualization of Maltose Uptake in Living Yeast Cells by Fluorescent Nanosensors, 2002, PNAS, 99:15, 9846-9851.*
Paul R. Steven, The Renaissance of Fluorescense Resonance Energy Transfer,2000, Nature Structural Biology, 7:9, pp. 730-734.*
BLAST result from SEQ ID No. 1, Dec. 29, 2011.*
Benson et al. "Design of bioelectronic interfaces by exploiting hinge-bending motions in proteins." Science 293: 1641-1644, 2001.
Blicharska et al. "Fluorescence quenching of Trp Repressor-Operator interaction." Journal of Protein Chemistry 18: 823-830, 1999.
Chen et al. "Protein localization in living cells and tissues using FRET and FLIM." Differentiation 71: 528-541, 2003.
D'Auria et al. "Enzyme fluorescence as a sensing tool: new perspectives in biotechnology." Curr. Opin. in Biotechnol. 12: 99-104, 2001.
De et al. "Novel biosensors for the detection of estrogen receptor ligands." Journal of Steroid Biochemistry and Molecular Biology 96: 235-244, 2005.
De Lorimier et al. "Construction of a fluorescent biosensor family." Protein Science 11: 2662, 2663, and 2670, 2002.
Deuschle et al. "Construction and optimization of a family of genetically encoded metabolite sensors by semirational protein engineering." Protein Science 14: 2304-2314, 2005.
Dwyer et al. "Periplamsic binding proteins: a versatile superfamily for protein engineering." Current Opinion in Structural Biology vol. 14, No. 4, 2004.
Fehr et al. "Visualization of maltose uptake in living yeast cells by fluorescent nanosonsor." PNAS 99: 9846-9851, 2002.
Gaits et al. "Shedding light on cell signaling: Interpretation of FRET biosensors." Science's STKE: signal transduction knowledge environment: 165 (PE3): 1-5, 2003.
Gu et al. "A novel analytical method for in vivo phosphate tracking." FEBS Lett. 580: 5885-5893, 2006.
Gunsalus et at. "Nucleotide sequence and expression of *Escherichia coli trpR*, the structural gene for the *trp* aporepressor." PNAS 77: 7117-7121, 1980.
Jenne et al. "Real-time characterization of ribozymes by fluorescence resonance energy transfer (FRET)." Angewandte Chemie 38: 1300-1303, 1999.
Mitra et al. "Fluorescence resonance energy transfer between blue-emitting and red-shifted excitation derivatives of the green fluorescent protein." Gene 173: 13-17, 1996.
Miyawaki et al. "Fluorescent indicators for Ca2+ based on green fluorescent proteins and clamodulin." Nature 388: 882-887, 1997.
Muyan et al. "Fusion estrogen receptor proteins: toward the development of receptor-based agonists and antagonists." Molecular and Cellular Endocrinology 182: 249-263.
Nagai et al. "A variant of yellow fluorescent protein with fast and efficient maturation for cell-biological application." Nature Biotechnology vol. 20, No. 1, 2002.
Okumoto et al. "Detection of glutamate release from neurons by genetically encoded surface-displayed FRET nanosensors." PNAS 102: 8740-8745, 2005.
Okumoto et al. "Genetically encoded sensors for ions and metabolites." Soil Sci. Plant Nutr. 50: 947-953, 2004.

(Continued)

*Primary Examiner* — Eileen B O Hara
(74) *Attorney, Agent, or Firm* — Morgan, Lewis & Bockius LLP

(57) ABSTRACT

Sucrose biosensors are disclosed, which comprise a sucrose binding domain conjugated to donor and fluorescent moieties that permit detection and measurement of Fluorescence Resonance Energy Transfer upon sucrose binding. Such biosensors are useful for real time monitoring of sucrose metabolism in living cells.

39 Claims, 3 Drawing Sheets

OTHER PUBLICATIONS

Salins et al. "Phosphate binding protein as the biorecognition element in a biosensor for phosphate." Sensors and Actuators B 97: 81-89, 2004.

Schafer et al. "X-ray structures of the maltose-maltodextrin-binding protein of the thermophilic bacterium *Alicyclobacillus acidocaldarius* provide insight into acid stability of proteins." J. Mol. Biol. 335: 261-274, 2004.

Sigmund "Viewpoint: are studies in genetically altered mice out of control?" Arterioscler. Thromb. Vasc. Biol. 20: 1425-1429, 2000.

Tanimura et al. "Fluorescent bionsensor for quantitative real-time measurements of inositol 1,4,5-triphosphate in single living cells." J. Biol. Chem. 279: 38095-38098, 2004.

Tolosa et al. "Glucose sensor for low-cost lifetime-based sensing using a genetically engineered protein." Analytical Biochemistry 267: 114-120, 1999.

Tsien "Building and breeding molecules to spy on cells and tumors." FEBS Lett. 579: 927-932, 2005.

Widersten et al. "Optimized heterologous expression of the polymorphic human glutathione transferase M1-1 based on silent mutations in the corresponding cDNA." Protein Expression and Purification 7: 367 371, 1996.

Wood et al. PRI-80 Database, Accession No. AI2966, Jul. 9, 2004, The Genome of the Natural Genetic Engineer Agrobacterium tumefaciens C58, Yoo et al. Science 294: 2317-2323, 2001.

Xu et al. "Kinetic and thermodynamic studies of purine repressor binding to corepressor and operator DNA." Journal of Biological Chemistry 273: 8058-8064, 1998.

Zhang et al. "Genetically encoded reporters of protein kinaso A activity reveal impact of substrate tethering." PNAS 98: 14997-15002, 2001.

* cited by examiner

A

B

C

SUCROSE BIOSENSORS AND METHODS OF USING THE SAME

STATEMENT OF GOVERNMENT SUPPORT

This work was supported by DOE grant No. DE-FG02-04ER15542. The government may have certain rights to this invention.

RELATED APPLICATIONS

The present application is a U.S. National Phase Application of International Application No. PCT/US2005/036951, filed Oct. 14, 2005, which is incorporated herein in its entirety.

This application is related to provisional application Ser. No. 60/643,576, provisional application Ser. No. 60/658,141, provisional application Ser. No. 60/658,142, provisional application Ser. No. 60/657,702, PCT application no. PCT/US2005/036955, and PCT application no. PCT/US2005/036953, which are herein incorporated by reference in their entireties.

FIELD OF INVENTION

The invention relates generally to the construction of sucrose biosensors and methods for measuring and detecting changes in sucrose levels using fluorescence resonance energy transfer (FRET).

BACKGROUND OF INVENTION

All publications and patent applications herein are incorporated by reference to the same extent as if each individual publication or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention.

Sucrose is the major transported form of carbohydrates in plants. Carbohydrate exporting tissue is often referred to as source tissue and the importing tissue as sink tissue. The most abundant carbon source transported into legume root nodules is photosynthetically produced sucrose. The transport mechanisms of sucrose in plants have been studied extensively and sucrose transporters from different plant species have been cloned and characterized. For example, the first sucrose transporter, SUT1, was cloned by functional expression in yeast (Riesmeier et al. 1992, EMBO J. 11: 4705-4713). Related genes from plants have since been obtained using the sequence for SUT1, including three genes from tomato (*Lycopersicon esculentum*). LeSUT1 and its orthologs from other plants are hydrophobic proteins consisting of 12 membrane spanning domains and are located in the plasma membrane of cells mediating highly specific influx of sucrose using a proton-coupled mechanism.

Even though a lot is known about how sucrose is being transported in the plant, less is known about the sucrose distribution in different compartments of the cell. No currently available technology addresses these issues in a satisfactory manner. For example, non-aqueous fractionation is static, invasive, has no cellular resolution and is sensitive to artifacts. While spectroscopic methods such as NMRi (nuclear magnetic resonance imaging) and PET (positron emission tomography) provide dynamic data, they have poor spatial resolution.

The development of genetically encoded molecular sensors, which transduce an interaction of the target molecule with a recognition element into a macroscopic observable signal, via allosteric regulation of one or more signaling elements, may provide answers to some of the questions. The recognition element may simply bind the target, bind and enzymatically convert the target, or may serve as a substrate for the target, as in the use of a specific target sequence in the construction of a protease sensor (Nagai and Miyawaki, 2004). The most common reporter element is a sterically separated donor-acceptor FRET pair of fluorescent proteins (GFP spectral variants or otherwise) (Fehr et al., 2002), although single fluorescent proteins (Doi and Yanagawa, 1999) or enzymes (Guntas and Ostermeier, 2004) are viable, as well. Some molecular sensors additionally employ a conformational actuator (most commonly a peptide which binds to one conformational state of the recognition element), to magnify the allosteric effect upon and resulting output of the reporter element (Miyawaki et al., 1997; Romoser et al., 1997; Kunkel et al., 2004).

The applicability of the method in the absence of a conformational actuator has recently been demonstrated, and its generalizability to a variety of analytes. Members of the bacterial periplasmic binding protein superfamily (PBPs) recognize hundreds of substrates with high affinity (atto- to low micro-molar) and specificity (Tam and Saier, 1993). PBPs have been shown by a variety of experimental techniques to undergo a significant conformational change upon ligand binding; fusion of an individual sugar-binding PBP with a pair of GFP variants produced sensors for maltose, ribose and glucose (Fehr et al., 2002; Fehr et al., 2003; Lager et al., 2003). The sensors were used to measure sugar uptake and homeostasis in living animal cells, and sub-cellular analyte levels were determined with nuclear-targeted versions (Fehr et al., 2004). The successful development of biosensors with bacterial PBPs for maltose, ribose, and glucose suggests to the present inventors that a similar strategy might be adopted to generate a biosensor specific for sucrose if suitable periplasmic sucrose binding proteins (BP) could be identified. A variety of periplasmic sugar binding proteins found in several microorganisms appear to have the potential for the sucrose sensor.

*Rhizobium meliloti* can occupy at least two distinct ecological niches: in soil as a free-living saprophyte, and as a nitrogen-fixing intracellular symbiont in root nodules of alfalfa and related legumes. AgpA encodes a periplasmic binding protein that is most similar to proteins from the periplasmic oligopeptide binding protein family. It is likely that agpA binds alpha-galactosides because alpha-galactosides induce the expression of agpA, and agpA mutants cannot utilize or transport these sugars. The agpA gene can be down-regulated by the syrA gene products and also by glucose and succinate. Activity of an agpA:TnphoA fusion protein is also downregulated by SyrA. Because syrA is known to be expressed at high levels in intracellular symbiotic *R. meliloti* and at low levels in the free-living bacteria, it has been hypothesized that agpA may belong to the class of gene products whose expression decreases when *R. meliloti* becomes an intracellular symbiont (Gage and Long 1998).

The *Sinorhizobium meliloti* agl operon encodes an alpha-glucosidase and a periplasmic-binding-protein-dependent transport system for alpha-glucosides. (Willis and Walker 1999). A cluster of six genes is involved in trehalose transport and utilization (thu) in *Sinorhizobium meliloti*. ThuE encodes the binding component of a binding protein-dependent trehalose/maltose/sucrose ABC transporter classified as a trehalose/maltose-binding protein (thuE). When the thuE locus is inactivated by gene replacement, the mutant *S. meliloti* strain was found to be impaired in its ability to grow on trehalose, and a significant retardation in growth was seen on maltose as well, while the wild type and the thuE mutant were indistinguishable for growth on glucose and sucrose. This suggested a possible overlap in function of the thuEFGK operon with the aglEFGAK operon, which was identified as a binding protein-dependent ATP-binding transport system for sucrose, maltose, and trehalose. ThuE expression is induced only by trehalose and not by cellobiose, glucose, maltopentaose, maltose, mannitol, or sucrose, suggesting that the thuEFGK system is primarily targeted toward trehalose. The aglEFGAK operon, on the other hand, is induced primarily by sucrose and to a lesser extent by trehalose (Jensen et al. 2002).

The *Agrobacterium tumefaciens* virulence determinant chvE is a periplasmic binding protein which participates in chemotaxis and virulence gene induction in response to monosaccharides which occur in the plant wound environment. The genes were named gguA, -B, and -C, for glucose galactose uptake. Mutations in gguA, gguB, or gguC do not affect virulence of *A. tumefaciens* on *Kalanchoe diagremontiana*; growth on 1 mM galactose, glucose, xylose, ribose, arabinose, fucose, or sucrose; or chemotaxis toward glucose, galactose, xylose, or arabinose (Kemner et al. 1997).

The thermoacidophilic gram-positive bacterium *Alicyclobacillus acidocaldarius* grows efficiently at 57° C. and pH 3.5. Uptake of radiolabeled maltose was inhibited by maltotetraose, acarbose, and cyclodextrins but not by lactose, sucrose, or trehalose. The corresponding binding protein (Aa-MalE) interacts with maltose with high affinity ($K_d$ of 1.5 µM). The purified wild-type and recombinant proteins bind maltose with high affinity over a wide pH range (2.5 to 7) and up to 80° C. (Hülsmann et al. 2000).

The extracellular, membrane-anchored trehalose/maltose-binding protein (TMBP) from the hyperthermophilic Archaeon *Thermococcus litoralis* has been crystallized and the structure was determined at 1.85 Å in complex with its substrate trehalose. TMBP is the substrate recognition site of the high-affinity trehalose/maltose ABC transporter. In vivo, this protein is anchored to the membrane, presumably via an N-terminal cysteine lipid modification. However, compared to maltose binding in MBP, direct hydrogen bonding between the substrate and the protein prevails while apolar contacts are reduced (Diez, 2001).

For none of these proteins had sucrose binding been shown directly. Furthermore, the *Agrobacterium* homolog of SmThuE had never been analyzed by mutation or by protein analysis. Thus, to develop sensors for sucrose, ThuE was isolated and tested.

SUMMARY OF INVENTION

The present inventors have surprisingly found that periplasmic sugar binding proteins from one of the bacterial species, *Agrobacterium tumefaciens*, may be used to construct biosensors for sucrose. The present invention thus provides sucrose biosensors that may be used for detecting and measuring changes in sucrose concentrations in living cells in general and plant cells in particular. Specifically, the invention provides an isolated nucleic acid which encodes a sucrose fluorescent indicator (SEQ ID NO: 3), the indicator comprising a sucrose binding protein moiety, a donor fluorescent protein moiety covalently coupled to the sucrose binding protein moiety, and an acceptor fluorescent protein moiety covalently coupled to the sucrose binding protein moiety (SEQ ID NO: 4), wherein fluorescence resonance energy transfer (FRET) between the donor moiety and the acceptor moiety is altered when the donor moiety is excited and sucrose binds to the sucrose binding protein moiety. Vectors, including expression vectors, and host cells comprising the inventive nucleic acids are also provided, as well as biosensor proteins encoded by the nucleic acids. Such nucleic acids, vectors, host cells and proteins may be used in methods of detecting sucrose binding and changes in levels of sucrose, and in methods of identifying compounds that modulate sucrose binding or sucrose-mediated activities.

DETAILED DESCRIPTION OF INVENTION

Figure 1:
FIG. 1 presents graphs of in vitro characterization of the sucrose sensor including substrate-induced FRET changes of nanosensors purified from BL21(DE3)gold. (A) Construct of the FLIPsuc sensor. (B) Spectra of the FLIPsuc sensor (fluorescent sucrose nanosensor with a $K_d$ for sucrose of 3.7 µM) at two different concentrations of sucrose: 0 µM and at 200 µM. (C) Sucrose, maltose, and glucose titration curves for FLIPsuc. The fitting curves are obtained by non-linear regression.
Figure 1:
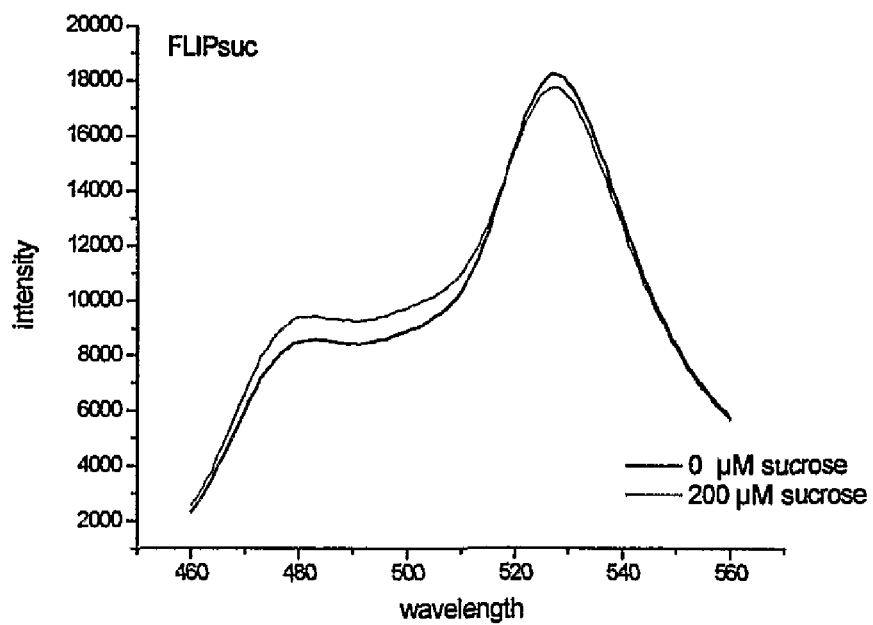
Figure 1:
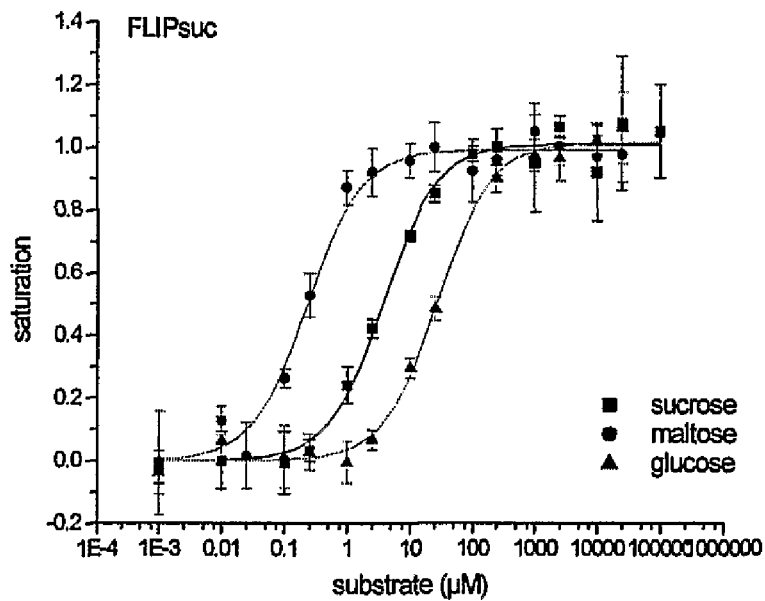

The following description includes information that may be useful in understanding the present invention. It is not an admission that any of the information provided herein is prior art or relevant to the presently claimed inventions, or that any publication specifically or implicitly referenced is prior art.

Other objects, advantages and features of the present invention become apparent to one skilled in the art upon reviewing the specification and the drawings provided herein. Thus, further objects and advantages of the present invention will be clear from the description that follows.

Biosensors

The present invention provides sucrose biosensors for detecting and measuring changes in sucrose concentrations using Fluorescence Resonance Energy Transfer (FRET).

In particular, the invention provides isolated nucleic acids encoding sucrose binding fluorescent indicators and the sucrose fluorescent indicators encoded thereby. One embodiment, among others, is an isolated nucleic acid which encodes a sucrose binding fluorescent indicator, the indicator comprising: a sucrose binding protein moiety, a donor fluorescent protein moiety covalently coupled to the sucrose binding protein moiety, and an acceptor fluorescent protein moiety covalently coupled to the sucrose binding protein moiety, wherein FRET between the donor moiety and the acceptor moiety is altered when the donor moiety is excited and sucrose binds to the sucrose binding protein moiety.

As used herein, "covalently coupled" means that the donor and acceptor fluorescent moieties may be conjugated to the ligand binding protein moiety via a chemical linkage, for instance to a selected amino acid in said ligand binding protein moiety. Covalently coupled also means that the donor and acceptor moieties may be genetically fused to the ligand binding protein moiety such that the ligand binding protein moiety is expressed as a fusion protein comprising the donor and acceptor moieties. As described herein, the donor and acceptor moieties may be fused to the termini of the sucrose binding moiety or to an internal position within the sucrose binding moiety so long as FRET between the donor moiety and the acceptor moiety is altered when the donor moiety is excited and sucrose binds to the sucrose binding protein moiety. For instance, see Provisional application 60/658,141, which is herein incorporated by reference.

A preferred sucrose binding protein moiety, among others, is a sucrose binding protein moiety from the *Agrobacterium tumefaciens* periplasmic sucrose binding protein (BP) having the sequence of SEQ ID NO: 2. Any portion of the sucrose BP sequence which encodes a sucrose binding region may be used in the nucleic acids of the present invention. Sucrose binding portions of sucrose BP or any of its homologues from other organisms, for instance Gram negative bacteria including thermophilic and hyperthermophilic organisms, may be cloned into the vectors described herein and screened for activity according to the disclosed assays.

Naturally occurring species variants of sucrose BP may also be used, in addition to artificially engineered variants comprising site-specific mutations, deletions or insertions that maintain measurable sucrose binding function. Variant nucleic acid sequences suitable for use in the nucleic acid constructs of the present invention will preferably have at least 30, 40, 50, 60, 70, 75, 80, 85, 90, 95, or 99% similarity or identity to the gene sequence for sucrose BP (SEQ ID NO: 1). Suitable variant nucleic acid sequences may also hybridize to the gene for sucrose BP under highly stringent hybridization conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), which is herein incorporated by reference. Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Preferred artificial variants of the present invention may be designed to exhibit decreased affinity for the ligand, in order to expand the range of ligand concentration that can be measured by the disclosed nanosensors. Additional artificial variants showing decreased or increased binding affinity for ligands may be constructed by random or site-directed mutagenesis and other known mutagenesis techniques, and cloned into the vectors described herein and screened for activity according to the disclosed assays. The binding specificity of disclosed biosensors may also be altered by mutagenesis so as to alter the ligand recognized by the biosensor. See, for instance, Looger et al., Nature, 423 (6936): 185-190.

The sensors of the invention may also be designed with a sucrose binding moiety and one or more additional protein binding moieties that are covalently coupled or fused together and to the donor and acceptor fluorescent moieties in order to generate an allosteric enzyme whose activity is controlled by more than one ligand. Allosteric enzymes containing dual specificity for more than one ligand have been described in the art, and may be used to construct the FRET biosensors described herein (Guntas and Ostermeier, 2004, J. Mol. Biol. 336(1): 263-73).

The isolated nucleic acids of the invention may incorporate any suitable donor and acceptor fluorescent protein moieties that are capable in combination of serving as donor and acceptor moieties in FRET. Preferred donor and acceptor moieties are selected from the group consisting of GFP (green fluorescent protein), CFP (cyan fluorescent protein), BFP (blue fluorescent protein), YFP (yellow fluorescent protein), and enhanced variants thereof, with a particularly preferred embodiment provided by the donor/acceptor pair CFP/YFP Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). An alternative is the MiCy/mKO pair with higher pH stability and a larger spectral separation (Karasawa S, Araki T, Nagai T, Mizuno H, Miyawaki A. Cyan-emitting and orange-emitting fluorescent proteins as a donor/acceptor pair for fluorescence resonance energy transfer. Biochem J. 2004 381:307-12). Also suitable as either a donor or acceptor is native DsRed from a Discosoma species, an ortholog of DsRed from another genus, or a variant of a native DsRed with optimized properties (e.g. a K83M variant or DsRed2 (available from Clontech)). Criteria to consider when selecting donor and acceptor fluorescent moieties is known in the art, for instance as disclosed in U.S. Pat. No. 6,197,928, which is herein incorporated by reference in its entirety.

As used herein, the term "variant" is intended to refer to polypeptides with at least about 30%, 40%, 50%, 60%, 70%, more preferably at least 75% identity, including at least 80%, 90%, 95% or greater identity to native fluorescent molecules. Many such variants are known in the art, or can be readily prepared by random or directed mutagenesis of native fluorescent molecules (see, for example, Fradkov et al., FEBS Lett. 479:127-130 (2000)). It is also possible to use or luminescent quantum dots (QD) for FRET (Clapp et al., 2005, J. Am. Chem. Soc. 127(4): 1242-50), dyes, including but not limited to TOTO dyes (Laib and Seeger, 2004, J. Fluoresc. 14(2):187-91), Cy3 and Cy5 (Churchman et al., 2005, Proc Natl Acad Sci USA. 102(5): 1419-23), Texas Red, fluorescein, and tetramethylrhodamine (TAMRA) (Unruh et al., Photochem Photobiol. 2004 Oct. 1), AlexaFluor 488, to name a few, as well as fluorescent tags (see, for example, Hoffman et al., 2005, Nat. Methods 2(3): 171-76).

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternative, one or more conservative substitutions that do not adversely affect the function of the fluorophores may also be incorporated. See PCT application PCT/US05/36953, "Methods of Reducing Repeat-Induced Silencing of Transgene Expression and Improved Fluorescent Biosensors], which is herein incorporated by reference in its entirety.

The invention further provides vectors containing isolated nucleic acid molecules encoding the biosensor polypeptides described herein. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the biosensor. Vectors may be adapted for function in a prokaryotic cell, such as $E.$ $coli$ or other bacteria, or a eukaryotic cell, including animal cells or plant cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, i.e., for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the sucrose binding domain or receptor between nucleic acids encoding donor and acceptor fluorescent molecules, resulting in expression of a chimeric or fusion protein comprising the sucrose binding domain covalently coupled to donor and acceptor fluorescent molecules. Exemplary vectors include the bacterial pRSET-FLIP derivatives disclosed in Fehr et al. (2002) (Visualization of maltose uptake in living yeast cells by fluorescent nanosensors, Proc. Natl. Acad. Sci. USA 99, 9846-9851), which is herein incorporated by reference in its entirety. Methods of cloning nucleic acids into vectors in the correct frame so as to express a fusion protein are well known in the art.

The sucrose biosensors of the present invention may be expressed in any location in the cell, including the cytoplasm, cell surface or subcellular organelles such as the nucleus, vesicles, ER, vacuole, etc. Methods and vector components for targeting the expression of proteins to different cellular compartments are well known in the art, with the choice dependent on the particular cell or organism in which the biosensor is expressed. See, for instance, Okumoto, S., Looger, L. L., Micheva, K. D., Reimer, R. J., Smith, S. J., and Frommer, W. B. (2005) $P$ $Natl$ $Acad$ $Sci$ $USA$ 102(24), 8740-8745; Fehr, M., Lalonde, S., Ehrhardt, D. W., and Frommer, W. B. (2004) $J$ $Fluoresc$ 14(5), 603-609, which are herein incorporated by reference in their entireties.

The chimeric nucleic acids of the present invention are preferably constructed such that the donor and acceptor fluorescent moiety coding sequences are fused to separate termini of the ligand binding domain in a manner such that changes in FRET between donor and acceptor may be detected upon ligand binding. Fluorescent domains can optionally be separated from the ligand binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of linkers or any of the fluorophores described herein may be used. For example, the inventors have shown that deleting N- or C-terminal portions of either of the three modules can lead to increased FRET ratio changes, as described in Application Ser. No. 60/658,141, which is herein incorporated by reference in its entirety.

It will also be possible depending on the nature and size of the sucrose binding domain to insert one or both of the fluorescent molecule coding sequences within the open reading frame of the sucrose binding protein such that the fluorescent moieties are expressed and displayed from a location within the biosensor rather than at the termini. Such sensors are generally described in U.S. Application Ser. No. 60/658,141, which is herein incorporated by reference in its entirety. It will also be possible to insert a sucrose binding sequence into a single fluorophore coding sequence, i.e. a sequence encoding a GFP, YFP, CFP, BFP, etc., rather than between tandem molecules. According to the disclosures of U.S. Pat. No. 6,469,154 and U.S. Pat. No. 6,783,958, each of which is incorporated herein by reference in their entirety, such sensors respond by producing detectable changes within the protein that influence the activity of the fluorophore.

The invention also includes host cells transfected with a vector or an expression vector of the invention, including prokaryotic cells, such as $E.$ $coli$ or other bacteria, or eukaryotic cells, such as yeast cells, animal cells or plant cells. As used herein, the term "plant" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. In another aspect, the invention features a transgenic non-human animal having a phenotype characterized by expression of the nucleic acid sequence coding for the expression of the environmentally stable biosensor. The phenotype is conferred by a transgene contained in the somatic and germ cells of the animal, which may be produced by (a) introducing a transgene into a zygote of an animal, the transgene comprising a DNA construct encoding the sucrose biosensor; (b) transplanting the zygote into a pseudopregnant animal; (c) allowing the zygote to develop to term; and (d) identifying at least one transgenic offspring containing the transgene. The step of introducing of the transgene into the embryo can be achieved by introducing an embryonic stem cell containing the transgene into the embryo, or infecting the embryo with a retrovirus containing the transgene. Transgenic animals of the invention include transgenic $C.$ $elegans$ and transgenic mice and other animals.

Transgenic plants are also included. Transgenic plants would be generated expressing the sensors by standard technologies such as *Agrobacterium*-mediated transformation and sensors would be targeted to the respective compartments, such as plastids, vacuole, cell surface etc using signal and anchoring sequences. Plants or tissues can then be analyzed for their steady state levels of sucrose in the compartment and changes in steady state levels in response to changes in the conditions, e.g., light, sugar supply, inhibitors or in various mutants can bet tested. This includes the analysis of mutant collections by high throughput screening or the analysis of cell lines or protoplasts.

The present invention also encompasses isolated sucrose biosensor molecules having the properties described herein, particularly sucrose binding fluorescent indicators constructed using hyperthermophilic and moderately thermophilic proteins. See e.g., provisional application 60/658,142, herein incorporated by reference in its entirety. Such polypeptides may be recombinantly expressed using the nucleic acid constructs described herein, or produced by chemically coupling some or all of the component domains. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle.

Methods of Detecting Sucrose

The nucleic acids and proteins of the present invention are useful for detecting sucrose binding and measuring changes in the levels of sucrose both in vitro and in a plant or an animal. In one embodiment, the invention comprises a method of detecting changes in the level of sucrose in a sample of cells, comprising (a) providing a cell expressing a nucleic acid encoding a sucrose biosensor as described herein and a sample of cells; and (b) detecting a change in FRET between a donor fluorescent protein moiety and an acceptor fluorescent protein moiety, each covalently attached to the sucrose binding domain, wherein a change in FRET between said donor moiety and said acceptor moiety indicates a change in the level of sucrose in the sample of cells.

FRET may be measured using a variety of techniques known in the art. For instance, the step of determining FRET may comprise measuring light emitted from the acceptor fluorescent protein moiety. Alternatively, the step of determining FRET may comprise measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. The step of determining FRET may also comprise measuring the excited state lifetime of the donor moiety or anisotropy changes (Squire A, Verveer P J, Rocks O, Bastiaens P I. J Struct Biol. 2004 July; 147(1):62-9. Red-edge anisotropy microscopy enables dynamic imaging of homo-FRET between green fluorescent proteins in cells.). Such methods are known in the art and described generally in U.S. Pat. No. 6,197,928, which is herein incorporated by reference in its entirety.

The amount of sucrose in a sample of cells can be determined by determining the degree of FRET. First the sensor must be introduced into the sample. Changes in sucrose concentration can be determined by monitoring FRET at a first and second time after contact between the sample and the fluorescent indicator and determining the difference in the degree of FRET. The amount of sucrose in the sample can be quantified for example by using a calibration curve established by titration.

The cell sample to be analyzed by the methods of the invention may be contained in vivo, for instance in the measurement of sucrose transport or signaling on the surface of cells, or in vitro, wherein sucrose efflux may be measured in cell culture. Alternatively, a fluid extract from cells or tissues may be used as a sample from which sucrose is detected or measured.

Methods for detecting sucrose levels as disclosed herein may be used to screen and identify compounds that may be used to modulate sucrose concentrations and activities relating to sucrose changes. In one embodiment, among others, the invention comprises a method of identifying a compound that modulates sucrose binding or levels comprising (a) contacting a mixture comprising a cell expressing an sucrose biosensor as disclosed herein and a sample of cells with one or more test compounds, and (b) determining FRET between said donor fluorescent domain and said acceptor fluorescent domain following said contacting, wherein increased or decreased FRET following said contacting indicates that said test compound is a compound that modulates sucrose binding activity or sucrose levels.

The term "modulate" in this embodiment means that such compounds may increase or decrease sucrose binding activity, or may affect activities, i.e., cell functions or signaling cascades, that affect sucrose levels. Compounds that increase or decrease sucrose binding activity may be targets for therapeutic intervention and treatment of disorders associated with aberrant sucrose activity, or with aberrant cell metabolism or signal transduction, as described above. Other compounds that increase or decrease sucrose binding activity or sucrose levels associated with cellular functions may be developed into therapeutic products for the treatment of disorders associated with ligand binding activity.

Utilities

The sucrose sensors of the present invention will be useful for a wide range of applications, e.g. to study sucrose levels in plants with better precision. Sucrose, as for many microorganisms, is an essential macronutrient for plant cells. The sensor will help elucidate the mechanisms for sucrose synthesis in plants and help the development of improved crops with better sucrose distribution. Such sensors would provide a unique opportunity to measure sucrose fluxes in living cells, e.g., to follow the exchange of sucrose between plants and microorganisms, the exchange between plants, the exchange of sucrose between plant cells, the subcellular distribution and fluxes of sucrose and the uptake of sucrose in the animal intestine. Such sensors may have value as tools to identify unknown functions such as sucrose effluxers, which are necessary for phloem loading to provide sucrose to the apoplasmic space before it can be imported by known sucrose transporters into the vascular tissue, to identify the transporters responsible for uptake and release of sucrose into/from intracellular compartments including the plastids and the vacuole and to identify the unknown regulators and the signaling cascades controlling sugar homeostasis. Thus, the sensor can be used to characterize cellular uptake and release, and more importantly intracellular compartmentation of sucrose.

The sensors can also be used to characterize the link between sucrose synthesis and plant growth and yield of specific plant cells, plant tissues, plant parts and plants as the growth response of a plant under a variety of different environmental conditions can be affected by carbon dioxide utilization, oxygen sensitivity, temperature-dependent growth responsiveness and expression of endogenous genes responsive to sugar content in general.

The sucrose sensors have further utility in the fresh produce and food industry. Nowadays, fresh produce quality is normally judged by its appearance, e.g., color, size, shape, presence and absence of diseases. The concentration of total soluble solids in the fresh produce is usually measured by a hand-held refractometer. Such assessment is usually inadequate in determining the overall quality of the fresh produce. For instance, it has been shown that there is poor correlation between total soluble solids and total sugar concentration, one of the main components that are important for flavor. Another important component for flavor is fruit acid. Fruit sugar/acid ratios can be used as an important index of consumer acceptability and act as one determinant of overall fruit quality. Thus the sensors may be applied in the routine analysis of sugar concentrations or sweetness of fresh produce and foods.

The sensors will be useful to study the biochemical pathways in vivo, i.e., to determine sucrose flux in microorganisms, in soil and also in eukaryotes. It can be used as a tool to develop new chemicals that positively or negatively affect sucrose synthesis in high throughput screens. The sucrose sensors of the present invention are excellent tools for drug discovery and screening. Sucrose levels may be measured in real time in response to chemicals, metabolic events, transport steps and signaling processes.

The sensors can also be used to diagnose diseases associated with sugar metabolism such as diabetes. They can also be used to diagnose certain diseases such as gastric epithelial damage. A method for detection of gastric epithelial damage, particularly ulcers and lesions in the stomach, using non-invasive, non-radioactive and non-x-ray techniques or procedures is disclosed in U.S. Pat. No. 5,620,899, herein incorporated by reference. This method employs a disaccharide which can be orally administered to a patient. The disaccharide does not transport across cell membranes, is metabolized within the small intestine to its monosaccharide components, and is not broken down elsewhere in the body. Damage to the gastric epithelium will allow the disaccharide to enter the blood without being metabolized. Hence, the disaccharide will appear in the blood or urine to an extent that can be correlated with the extent of gastric epithelial damage. Typically, the disaccharide is administered to a patient, followed by collection of blood or urine, which is assayed for the disaccharide. The use of sucrose in particular as a diagnostic marker in detection of gastric epithelial damage is described in U.S. Pat. No. 5,605,840, herein incorporated by reference. Thus, the sucrose sensors may provide tools to investigate the underlying defects and to develop cures.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Cloning and Structural Modeling of Sucrose BP

We first hypothesized that the maltose/trehalose/sucrose binding protein *Sinorhizobium meliloti* (SmThuE) is also responsible for the transport of sucrose. Moreover, database searches identified an *Agrobacterium tumefaciens* protein related to the putative *Sinorhizobium meliloti* maltose/trehalose/sucrose binding protein (SmThuE) To generate a sucrose sensor, SmThuE was fused with two GFP variants by attaching a cyan (CFP) and a yellow fluorescent protein (YFP) to the N- and C-termini of the binding protein. However, the fusion protein of SmThuE was found to be unstable when flanked with ECFP and EYFP.

Because the maltose/trehalose/sucrose binding protein from *Agrobacterium tumefaciens* (AtThuE) is 78.9% identical over predicted mature region of the SmThuE protein (SEQ ID NO: 2) and is 21.4% homologous to the maltose binding protein from *E. coli* (malE), we attempted to clone the AtThuE binding protein. To isolate the gene, a PCR product from genomic *Agrobacterium tumefaciens* (strain C58C1) DNA encoding mature AtThuE without signal sequence and stop codon was cloned into the KpnI site between ECFP and EYFP genes (FIG. 1A). The chimeric gene was inserted into pRSET (Invitrogen) and transferred to *E. coli* BL21(DE3) Gold (Stratagene). The AtThuE sequence (SEQ ID NO: 1) was confirmed by DNA sequencing and was found to carry a $N_{192}D$ substitution compared to the published sequence. It is unknown whether this difference corresponds to a mutation or natural variation. Since $N_{192}D$ was outside the binding pocket and since AtThuE carrying the mutation was functional as a sugar sensor (see Table 1), all further experiments were carried out with the nanosensor named FLIPsuc4µ carrying the mutation $N_{192}D$. FLIPsuc proteins were extracted from BL21(DE3)gold and purified as described (Fehr et al. 2002).

Example 2

In vitro Characterization of Nanosensors

A DNA fragment encoding the mature *Agrobacterium tumefaciens* maltose/trehalose/sucrose BP protein was fused between the ECFP and EYFP sequences as described above. The chimeric gene was expressed in *E. coli* and the protein product purified and assayed for substrate specificity.

Substrate titration curves and substrate specificity analysis were performed on Safire (Tecan) fluorometer. ECFP was excited at 433 nm and emission was set to 485 nm and 528 nm for ECFP and EYFP, respectively (bandwidth 12 nm). All in vitro analyses were performed in 20 mM MOPS buffer at pH 7. FRET was determined as EYFP-ECFP emission intensity ratio. Using the change in ratio upon ligand binding, binding constants ($K_d$) were determined by fitting substrate titration curves to equation 1: $S=1-(r-r_{min})(r_{max}-r_{min})=[S]_b/[P]_t=n[S]/(K_d+[S])$, where [S] is substrate concentration; $[S]_b$, concentration of bound substrate; n, number of binding sites; $[P]_t$, total concentration of binding protein; r, ratio; $r_{min}$, minimum ratio in absence of ligand; $r_{max}$, maximum ratio at saturation. Hill coefficients were determined using Hill equation 2: $S=(n[S]^n)/(K_d+[S]^n)$.

Due to similarity of the relative position of the termini to the hinge region of this sensor and the malE sensor, we predicted that the sugar-induced hinge-twist motion would move the GFP-variants closer together, causing an increase in FRET. Surprisingly, addition of sugar to the purified protein resulted in a decrease in FRET. The same phenomenon was observed in unrelated ribose (FLIPrib) and glucose sensors (FLIPglu). Thus, titration of the purified fusion protein FLIPsuc4µ displayed a sucrose concentration-dependent decrease in FRET (FIG. 1B). The binding constant ($K_d$) of this sensor for sucrose was determined to be 3.7 µM and the Hill coefficient was 1.04. As shown in Table 1, the maximum ratio change observed for FLIPsuc is 0.2. FLIPsuc4, permits sucrose quantification in the high-affinity range between 0.4 µM to 33 µM.

Since trehalose binding protein from Thermus also binds other sugars, we tested the specificity of the FLIPsuc sensor (Silva et al. 2005). To determine the relative specificity of the sensor, we compared the affinity of the sensor for maltose, glucose, and sucrose (FIG. 1C). We found that the affinity of the sensor for maltose is higher and the affinity for glucose is in the same range as that for sucrose. These data suggest that while it is possible to use FLIPsuc to measure sucrose levels, the FLIPsuc sensor overlaps in function with the maltose (FLIPmal) and glucose (FLIPglu) sensors. Therefore, it is desirable to develop a FLIPsuc sensor with enhanced selectivity and specificity for sucrose.

Example 3

Generation of Mutant FLIPsuc with Altered Specificity

To expand the dynamic range of the sucrose sensor, site directed mutagenesis was used as described above to lower the binding affinity of the sucrose binding domain. Affinity mutants of FLIPsuc4μ were generated. Alignment together with modeling of AtThuE with maltose binding proteins that have been crystallized helped predict residues important for ligand binding. Mutation of amino acids predicted to reside in the sucrose binding site of FLIPsuc4μ generated a set of sensors that were sensitive over a broad range of sucrose concentrations, with significantly greater maximum ratio changes upon sucrose binding (see Table 1). Mutant forms carrying substitutions $F_{113}A$, $D_{115}A$, $D_{115}E$, $D_{115}N$, $W_{244}A$, $Y_{246}A$ and $W_{283}A$ were generated using Kunkel mutagenesis (Kunkel et al. 1991) in the mutant background of FLIPsuc41t. The affinity mutants were designated as FLIPsucF113A, FLIPsucW283A, FLIPsucD115A, FLIPsucD115E, FLIPsucY246A, and FLIPsucW244A. All six mutants have lower affinities for sucrose than that of FLIPsuc4μ, with a $K_d$ value varying from 10 μM to the higher mM range (Table 1). The starting ratio between EYFP and ECFP ranges from 1.4 to close to 2.0, which is also similar to what has been seen in other sugar sensors (FLIPmal, FLIPglu and FLIPrib). Introducing substitution $F_{113}A$ into the ThuE moiety of FLIPsuc4μ produced FLIPsuc10μ, which has a binding constant ($K_d$) of 10 μM for sucrose, thus providing a range for sucrose quantification between at least 1 μM and 90 μM (Table 1).

Figure 2:
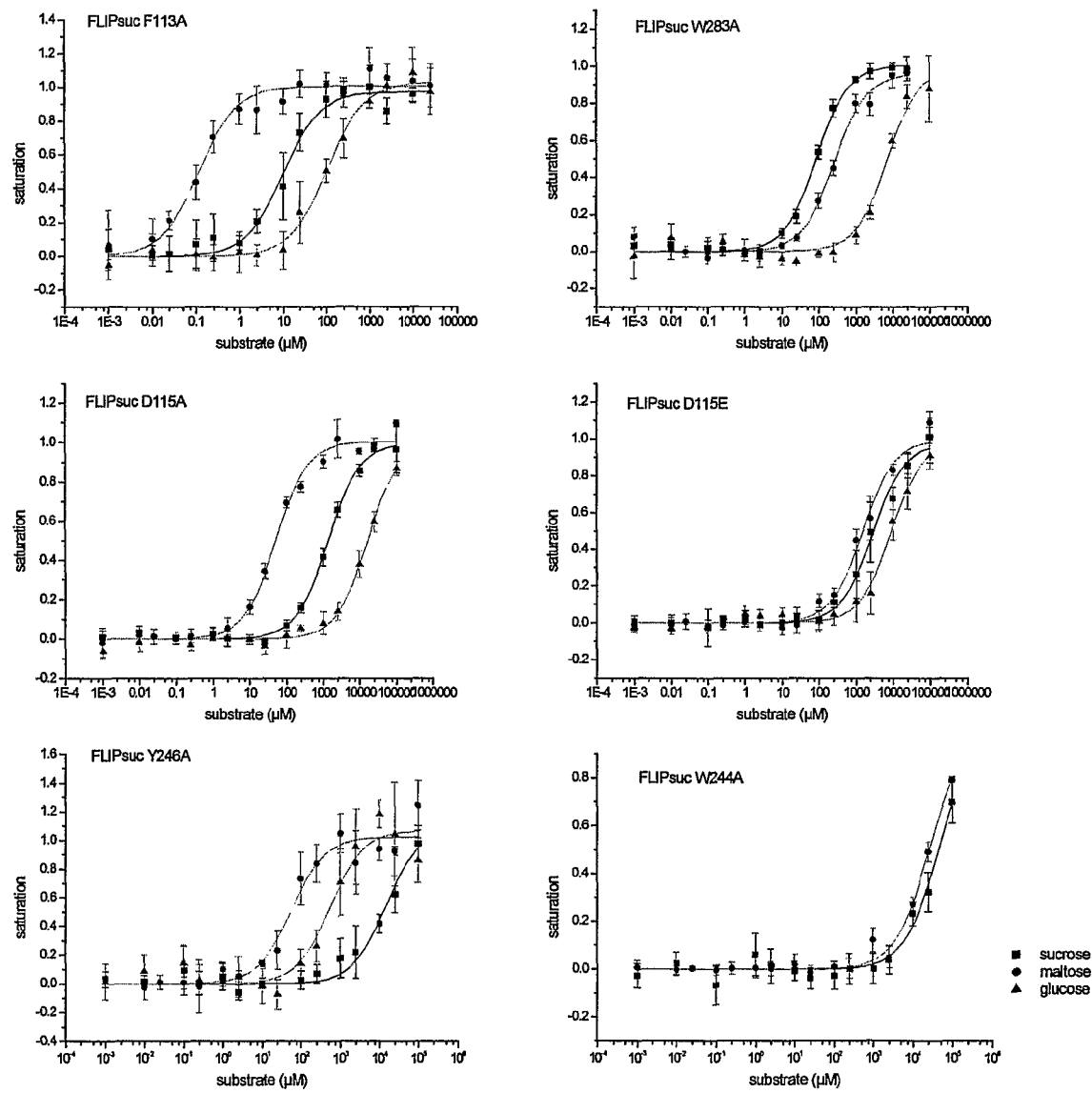
FIG. 2 contains graphs showing the results of binding specificity assays for the affinity mutants. All the sensors were titrated with solutions of sucrose, maltose and glucose. The mutants are FLIPsuc F113A, FLIPsuc W283A, FLIPsuc D115A, FLIPsuc D115E, FLIPsuc Y246A, and FLIPsuc W224A.

One important factor for a good sensor is its delta ratio, a measure of change in ratio from no binding to saturated binding. The higher the change in ratio the easier small changes in the sugar level can be measured accurately. FLIPsuc4μ has a delta ratio of approximately 0.2. FLIPsuc-10μ has less of a change (0.1-0.15) while the sensor carrying the $D_{115}A$ mutation has an improved delta ratio of at least 0.6. The $D_{115}A$ mutation gives a sensor with a $K_d$ for sucrose of 1.4 mM. According to the crystal structure model of AtThuE, position $D_{115}$ is located in the hinge region of the binding protein pocket. The $D_{115}$ residue was not only changed to an alanine but also to glutamate and asparagine. The $D_{115}N$ substitute created a sensor where a change in ratio upon addition of sucrose was no longer seen, while a change from aspartate to glutamate gave a sensor with a $K_d$ of 2.9 mM and a delta ratio of almost 0.4 (FIG. 2, Table 1).

Figure 3:
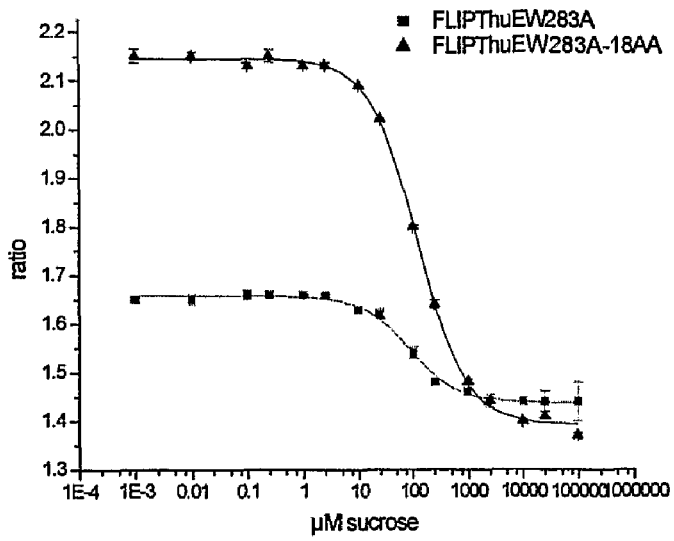
FIG. 3 is a graph showing improved delta ratio of FLIPThuEW283A-18AA, a sucrose sensor that is 18 amino acids shorter in the linker sequence than FLIPThuEW283A.

In an attempt to improve the delta ratio of the sucrose sensor the sensor containing the W283A mutation was cloned into a construct with a shorter linker sequence between the GFP variants and the binding protein. Deuschle et al. (2005) has shown that the length of the linker sequence plays a major role in the maximum change in ratio. A construct corresponding to FLIPglu600μΔ5 was constructed which gives a sucrose sensor whose linker was shortened by 18 amino acids (FLIPsucW283A-18AA). The construct provided a sensor with a 3-fold higher ratio change than the original construct (FIG. 3).

TABLE 1

FLIP sucrose affinity mutants. Binding constants determined in vitro.

| Nanosensor | Mutation | Sucrose | | maltose | | glucose | |
|---|---|---|---|---|---|---|---|
| | | $K_d$ (μM) | Δratio | $K_d$ (μM) | Δratio | $K_d$ (μM) | Δratio |
| FLIPsuc4μ | wt | 3.7 | 0.18 | 0.23 | 0.21 | 27 | 0.18 |
| FLIPsuc10μ | F113A | 10 | 0.12 | 0.12 | 0.12 | 106 | 0.12 |
| FLIPsuc88μ | W283A | 88 | 0.29 | 265 | 0.25 | 7210 | 0.21 |
| FLIPsuc1m | D115A | 1350 | 0.68 | 51 | 0.37 | 16200 | 0.50 |
| FLIPsuc3m | D115E | 2870 | 0.36 | 1530 | 0.39 | 9110 | 0.44 |
| FLIPsuc15m | Y246A | 14600 | 0.14 | 56 | 0.14 | 554 | 0.07 |
| FLIPsuc46m | W244A | 46200 | 0.4 | 26500 | 0.42 | — | — |

Example 4

Substrate Binding Specificity

Measuring substrate concentration in complex mixtures (e.g. cytoplasm of a living cell) requires sensors with high specificity towards their substrate. Therefore, for in vivo applications, it is necessary to test the binding specificity of each of the sensors.

Figure 4:
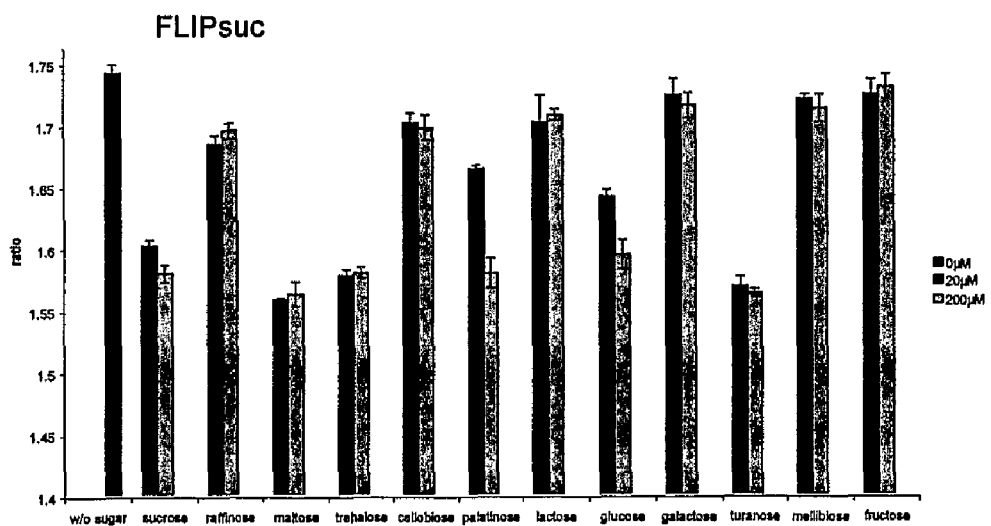
FIG. 4 shows substrate specificity of the FLIPsuc sensor.

SmThuE is mainly functioning as a trehalose and maltose binding protein. Sucrose is thought to be transported to a lesser extent. FLIPsuc4μ was therefore incubated with trehalose, maltose and other related sugars to test for its binding capacities. Substrate-induced conformational changes were measured using FRET in micro plate assays. FLIPsuc4μ binds maltose, trehalose and turanose at 5× $K_d$ (20 μM) to the same extent or better than sucrose and glucose and palatinose to lesser extent (FIG. 4). Fructose, galactose and cellobiose were not recognized even after addition of higher sugar concentrations (50× $K_d$). Maltose and glucose were chosen for further analysis of FLIPsuc4μ and its mutants since they are important sugars in plants and might therefore interfere with sucrose measurements in vivo. FLIPsuc4μ shows a higher affinity for maltose ($K_d$ 230 nM) than for sucrose, which is consistent with the involvement of SmThuE primarily in maltose and trehalose uptake and to a lesser extent in sucrose uptake (Jensen et al.). Glucose has less affinity for the sensor, with a $K_d$ of 27 μM. Most mutants show similar patterns with higher affinity for maltose than sucrose. FLIPsuc-10μ is the most significant example with an 83 times higher affinity for maltose than sucrose (Table 1). The $D_{115}$ mutants both show the highest affinity for maltose compared to sucrose and maltose, but to a different extent. While FLIPsucD115A has a $K_d$ of 51 μM for maltose and 16 mM for glucose, the $K_d$ values for FLIPsucD115E are less spread, with 1.5 mM for maltose and 9.1 mM for glucose. However, FLIPsucW283A shows a different pattern with the affinity for sucrose being three times higher than for maltose ($K_d$ 265 μM) and a $K_d$ for glucose of 7.2 mM.

Thus FLIPsucW283A surprisingly shows a much better selectivity for sucrose and thus is best suited for in vivo applications since the data will be showing mainly changes of sucrose and not be so much affected by changes in other sugars such as glucose or maltose. Further mutants can be generated that retain the specificity but have lower affinity for the in vivo analysis.

All publications, patents and patent applications discussed herein are incorporated herein by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Diez, J., Diederichs, K., Greller, G., Horlacher, R., Boos, W., and Welte, W. 2001. The crystal structure of a liganded trehalose/maltose-binding protein from the hyperthermophilic Archaeon *Thermococcus litoralis* at 1.85 ANG. *J. Mol. Biol.* 305: 905-915.

Fehr, M., Frommer, W. B., and Lalonde, S. 2002. Visualization of maltose uptake in living yeast cells by fluorescent nanosensors. *Proceedings of the National Academy of Sciences of the USA* 99: 9846-9851.

Gage, D. J., and Long, S. R. 1998. alpha-Galactoside uptake in *Rhizobium meliloti*: isolation and characterization of agpA, a gene encoding a periplasmic binding protein required for melibiose and raffinose utilization. *J. Bacteriol.* 180: 5739-5748.

Hülsmann, A., Lurz, R., Scheffel, F., and Schneider, E. 2000. Maltose and maltodextrin transport in the thermoacidophilic gram-positive bacterium *Alicyclobacillus acidocaldarius* is mediated by a high-affinity transport system that includes a maltose binding protein tolerant to low pH. *J. Bacteriol.* 182: 6292-6301.

Jensen, J. B., Peters, N. K., and Bhuvaneswari, T. V. 2002. Redundancy in periplasmic binding protein-dependent transport systems for trehalose, sucrose, and maltose in *Sinorhizobium meliloti*. *J. Bacteriol.* 184: 2978-2986.

Johnson, J. M., and Church, G. M. 2000. Predicting ligand-binding function in families of bacterial receptors. *Proceedings of the National Academy of Sciences of the USA* 97: 3965-3970.

Kemner, J. M., Liang, X., and Nester, E. W. 1997. The *Agrobacterium tumefaciens* virulence gene chvE is part of a putative ABC-type sugar transport operon. *J. Bacteriol.* 179: 2452-2458.

Kunkel, T. A., Bebenek, K., and McClary, J. 1991. Efficient site-directed mutagenesis using uracil-containing DNA. *Methods Enzymol.* 204: 125-139.

Mowbray, S. L., and Cole, L. B. 1992. 1.7 A X-ray structure of the periplasmic ribose receptor from *Escherichia coli*. *Journal of Molecular Biology* 225: 155-175.

Silva, Z., Sampaio, M. M., Henne, A., Bohm, A., Gutzat, R., Boos, W., da Costa, M. S., and Santos, H. 2005. The high-affinity maltose/trehalose ABC transporter in the extremely thermophilic bacterium *Thermus thermophilus* HB27 also recognizes sucrose and palatinose. *J. Bacteriol.* 187: 1210-1218.

Willis, L. B., and Walker, G. C. 1999. A novel *Sinorhizobiuni meliloti* operon encodes an alpha-glucosidase and a periplasmic-binding-protein-dependent transport system for alpha-glucosides. *J. Bacteriol.* 181: 4176-4184.

What is claimed:

1. An isolated nucleic acid which encodes a sucrose fluorescent indicator, the indicator comprising:
   a sucrose binding protein moiety which is encoded by a nucleic acid sequence with at least 85% identity to SEQ ID NO: 1;
   a donor fluorescent protein moiety covalently coupled to the sucrose binding protein moiety; and
   an acceptor fluorescent protein moiety covalently coupled to the sucrose binding protein moiety;
   wherein fluorescence resonance energy transfer (FRET) between the donor moiety and the acceptor moiety is altered when the donor moiety is excited and sucrose binds to the sucrose binding protein moiety.

2. The isolated nucleic acid of claim 1, wherein the donor and acceptor moieties are genetically fused to said sucrose binding protein moiety.

3. The isolated nucleic acid of claim 2, wherein the donor and acceptor moieties are genetically fused to the termini of said sucrose binding protein moiety.

4. The isolated nucleic acid of claim 2, wherein one or both the donor and acceptor moieties are genetically fused to an internal position of said sucrose binding protein moiety.

5. The isolated nucleic acid of claim 1, wherein said sucrose binding protein moiety is a bacterial periplasmic binding protein (PBP) moiety.

6. The isolated nucleic acid of claim 5, wherein said bacterium is a species of *Agrobacterium*.

7. The isolated nucleic acid of claim 6, wherein said sucrose binding protein moiety is from sucrose BP of *Agrobacterium*.

8. The isolated nucleic acid of claim 7, wherein said sucrose binding protein moiety has the sequence of SEQ ID No. 2.

9. The isolated nucleic acid of claim 1, wherein said donor fluorescent protein moiety is selected from the group consisting of a GFP, a CFP, a BFP, a YFP, a dsRED, CoralHue Midoriishi-Cyan (MiCy) and monomeric CoralHue Kusabira-Orange (mKO).

10. The isolated nucleic acid of claim 1, wherein said acceptor fluorescent protein moiety is selected from the group consisting of a GFP, a CFP, a BFP, a YFP, a dsRED, CoralHue Midoriishi-Cyan (MiCy) and monomeric CoralHue Kusabira-Orange (mKO).

11. The isolated nucleic acid of claim 1, wherein said donor fluorescent protein moiety is a CFP and said acceptor fluorescent protein moiety is YFP Venus.

12. The isolated nucleic acid of claim 1, further comprising at least one linker moiety.

13. The isolated nucleic acid of claim 1, wherein said sucrose fluorescent indicator shows increased or decreased affinity for sucrose compared with a fluorescent indicator comprising the polypeptide of SEQ ID NO: 2.

14. The isolated nucleic acid of claim 1, wherein said sucrose fluorescent indicator shows an increase in maximum FRET ratio change compared with a fluorescent indicator comprising the polypeptide of SEQ ID NO: 2.

15. A cell expressing the nucleic acid of claim 1.

16. The cell of claim 15, wherein the sucrose fluorescent sensor is expressed in the cytosol of said cell.

17. The cell of claim 15, wherein the sucrose fluorescent sensor is expressed on the surface of said cell.

18. The cell of claim 15, wherein the sucrose fluorescent sensor is expressed in the nucleus of said cell.

19. The cell of claim 15, wherein the cell is a prokaryote.

20. The cell of claim 15, wherein the cell is a eukaryotic cell.

21. The cell of claim 20, wherein the cell is a yeast cell.

22. The cell of claim 15, wherein the cell is a plant cell.

23. An expression vector comprising the nucleic acid of claim 1.

24. A cell comprising the vector of claim 23.

25. The expression vector of claim 23 adapted for function in a prokaryotic cell.

26. The expression vector of claim 23 adapted for function in a eukaryotic cell.

27. A transgenic plant expressing the nucleic acid of claim 1.

28. A sucrose binding fluorescent indicator encoded by the nucleic acid of claim 1.

29. A method of detecting changes in the level of sucrose in a sample of cells, comprising:
   (a) providing a cell expressing the nucleic acid of claim 1; and
   (b) detecting a change in FRET between said donor fluorescent protein moiety and said acceptor fluorescent protein moiety,
   wherein a change in FRET between said donor moiety and said acceptor moiety indicates a change in the level of sucrose in a sample of cells.

30. The method of claim 29, wherein the step of determining FRET comprises measuring light emitted from the acceptor fluorescent protein moiety.

31. The method of claim 29, wherein determining FRET comprises measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety.

32. The method of claim 29, wherein the step of determining FRET comprises measuring the excited state lifetime of the donor moiety.

33. The method of claim 29, wherein said sample of cells is contained in vivo.

34. The method of claim 29, wherein said sample of cells is contained in vitro.

35. A method of identifying a compound that modulates the binding of a sucrose to its receptor, comprising:
   (a) contacting a cell expressing the nucleic acid of claim 1 with one or more test compounds in the presence of sucrose; and
   (b) determining FRET between said donor fluorescent domain and said acceptor fluorescent domain following said contacting,
   wherein increased or decreased FRET following said contacting indicates that said test compound is a compound that modulates sucrose binding.

36. The isolated nucleic acid of claim 1, wherein the sucrose binding moiety is encoded by a nucleic acid comprising at least 95% identity to SEQ ID NO: 1.

37. The isolated nucleic acid of claim 1, wherein the sucrose binding moiety is encoded by a nucleic acid consisting of at least 95% identity to SEQ ID NO: 1.

38. The isolated nucleic acid of claim 1, wherein the sucrose binding moiety is encoded by a nucleic acid comprising SEQ ID NO: 1.

39. The isolated nucleic acid of claim 1, wherein the sucrose binding moiety is encoded by a nucleic acid consisting of SEQ ID NO: 1.

* * * * *

SEQUENCE LISTING

<160> NUMBER OF SEQ ID NOS: 4

<210> SEQ ID NO 1
<211> LENGTH: 1359
<212> TYPE: DNA
<213> ORGANISM: Agrobacterium tumefaciens

<400> SEQUENCE: 1

```
ttgacagatt gttcagcttt tgcgagcctt ccttcagtca aaagcgcttt caattttgag      60
gacaatcggg agcgtcaacg gaggagtttg acaatgaata tttccatgaa gactttgttc     120
ctgtgcggag tcgcgttttc cgccgccatt tcggctgagg cggccgaact ttccattgcc     180
gcaaattcga ccggcaagaa cgtcgcgttt ttccgcgaac gcatcgccgc tttcgagaaa     240
gagaccggtc acaaggtcaa tctcgtcacc atgccgtctt cttccagcga acagttcagc     300
cagtaccggc tgtggcttgc cgccggcaac aaggatgtcg acgtttacca gacggacgtg     360
atctgggccc cgcagctagc cgaacaattc gtggatttga ccgcagcgac caaggatgtc     420 atcgggatc atttcccttc tatcgtcgcc tcacagacgg tggacggcaa gctcgtcgcc     480
atgccgatgt tcaccgacgc gccggcgctg ttttaccgca aggaccttct ggaaaaatat     540
ggcaagcagc cgccgaaaac ctggaaggaa ctgagcgaga ccgccaagga ggttcaggac     600
aaggaacgcg cggccggcca gaaggacctc tggggcttcg ttttcaggg cagcgcctat     660 gaaggtctga cctgcaacgc tctggaatgg atcgcatccg cgggcggtgg ccatatcgtt     720
```

```
gaaaccaacg gcgatatctc catcaataac gagaaggcgg cagctgcaat cgaaaccgcc      780
aaaggctggg tcggcaccat cgcaccgcag ggcgttctcg cttacaagga agaggaagca      840
cgcggtgtct ggcagaccgg caattccgtc ttcatgcgca actggcccta tgcctatgcg      900
cttggaaatg gtgccgacag cgcgatcaag acaagttcg gcgtcacgcc gctgccggca       960
ggtgaagaag gcgcagcccc cgcttccaca ctcggcggct ggaaccttgc tgtttcgaaa     1020
tattccgacg atcaggaagc ggctatccag ctggtaaaat tcctggcatc aaaggatacc     1080
cagaagctgc gcgcgatcca gctgtccaac atgccgacga tcgcttcgct ttacgacgac     1140
aaggatgtcg cggccgcaca gcccttcatg ccgacgtgga gccgatctt cgagaccgcc      1200 gttccgcgtc cttccgcctc ggccaaggtg aaatataacg aggtttcggc caagttctgg     1260
ggcgccgtgc acaacacgct ctccggcaat ggtacggcgg cggaaaatct cgaacttctc     1320
gaggttgaac tgaccgatct caaaggcaac ggctggtaa                             1359
```

<210> SEQ ID NO 2
<211> LENGTH: 452
<212> TYPE: PRT
<213> ORGANISM: Agrobacterium tumefaciens

<400> SEQUENCE: 2

```
Met Thr Asp Cys Ser Ala Phe Ala Ser Leu Pro Ser Val Lys Ser Ala
1               5                   10                  15

Phe Asn Phe Glu Asp Asn Arg Glu Arg Gln Arg Arg Ser Leu Thr Met
            20                  25                  30

Asn Ile Ser Met Lys Thr Leu Phe Leu Cys Gly Val Ala Phe Ser Ala
        35                  40                  45

Ala Ile Ser Ala Glu Ala Ala Glu Leu Ser Ile Ala Ala Asn Ser Thr
    50                  55                  60

Gly Lys Asn Val Ala Phe Phe Arg Glu Arg Ile Ala Ala Phe Glu Lys
65                  70                  75                  80

Glu Thr Gly His Lys Val Asn Leu Val Thr Met Pro Ser Ser Ser Ser
                85                  90                  95

Glu Gln Phe Ser Gln Tyr Arg Leu Trp Leu Ala Ala Gly Asn Lys Asp
            100                 105                 110

Val Asp Val Tyr Gln Thr Asp Val Ile Trp Ala Pro Gln Leu Ala Glu
        115                 120                 125

Gln Phe Val Asp Leu Thr Ala Ala Thr Lys Asp Val Ile Gly Asp His
    130                 135                 140

Phe Pro Ser Ile Val Ala Ser Gln Thr Val Asp Gly Lys Leu Val Ala
145                 150                 155                 160

Met Pro Met Phe Thr Asp Ala Pro Ala Leu Phe Tyr Arg Lys Asp Leu
                165                 170                 175

Leu Glu Lys Tyr Gly Lys Gln Pro Pro Lys Thr Trp Lys Glu Leu Ser
            180                 185                 190

Glu Thr Ala Lys Glu Val Gln Asp Lys Glu Arg Ala Ala Gly Gln Lys
        195                 200                 205

Asp Leu Trp Gly Phe Val Phe Gln Gly Ser Ala Tyr Glu Gly Leu Thr
    210                 215                 220

Cys Asn Ala Leu Glu Trp Ile Ala Ser Ala Gly Gly His Ile Val
225                 230                 235                 240

Glu Thr Asn Gly Asp Ile Ser Ile Asn Asn Glu Lys Ala Ala Ala Ala
                245                 250                 255

Ile Glu Thr Ala Lys Gly Trp Val Gly Thr Ile Ala Pro Gln Gly Val
            260                 265                 270
```

```
Leu Ala Tyr Lys Glu Glu Ala Arg Gly Val Trp Gln Thr Gly Asn
            275                 280                 285

Ser Val Phe Met Arg Asn Trp Pro Tyr Ala Tyr Ala Leu Gly Asn Gly
        290                 295                 300

Ala Asp Ser Ala Ile Lys Asp Lys Phe Gly Val Thr Pro Leu Pro Ala
305                 310                 315                 320

Gly Glu Glu Gly Ala Ala Pro Ala Ser Thr Leu Gly Gly Trp Asn Leu
            325                 330                 335

Ala Val Ser Lys Tyr Ser Asp Asp Gln Glu Ala Ala Ile Gln Leu Val
            340                 345                 350

Lys Phe Leu Ala Ser Lys Asp Thr Gln Lys Leu Arg Ala Ile Gln Leu
            355                 360                 365

Ser Asn Met Pro Thr Ile Ala Ser Leu Tyr Asp Asp Lys Asp Val Ala
        370                 375                 380

Ala Ala Gln Pro Phe Met Pro Thr Trp Lys Pro Ile Phe Glu Thr Ala
385                 390                 395                 400

Val Pro Arg Pro Ser Ala Ser Ala Lys Val Lys Tyr Asn Glu Val Ser
            405                 410                 415

Ala Lys Phe Trp Gly Ala Val His Asn Thr Leu Ser Gly Asn Gly Thr
            420                 425                 430

Ala Ala Glu Asn Leu Glu Leu Leu Glu Val Glu Leu Thr Asp Leu Lys
            435                 440                 445

Gly Asn Gly Trp
450

<210> SEQ ID NO 3
<211> LENGTH: 2676
<212> TYPE: DNA
<213> ORGANISM: Artificial Sequence
<220> FEATURE:
<223> OTHER INFORMATION: DNA sequence of sucrose biosensor gene

<400> SEQUENCE: 3
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cccctgacct gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagggt     720
ggtaccggag cgccgctga gcggccgaa ctttccattg ccgcaaattc gaccggcaag     780
aacgtcgcgt ttttccgcga acgcatcgcc gctttcgaga aagagaccgg tcacaaggtc     840
aatctcgtca ccatgccgtc ttcttccagc gaacagttca gccagtaccg gctgtggctt     900
gccgccggca caaggatgt cgacgtttac cagacggacg tgatctgggc cccgcagcta     960
gccgaacaat tcgtggattt gaccgcagcg accaaggatg tcatcgggga tcatttccct    1020
```

-continued

```
tctatcgtcg cctcacagac ggtggacggc aagctcgtcg ccatgccgat gttcaccgac    1080
gcgccggcgc tgttttaccg caaggacctt ctggaaaaat atggcaagca gccgccgaaa    1140
acctggaagg aactgagcga gaccgccaag gaggttcagg acaaggaacg cgcggccggc    1200
cagaaggacc tctggggctt cgttttcag ggcagcgcct atgaaggtct gacctgcaac    1260
gctctggaat ggatcgcatc cgcgggcggt ggccatatcg ttgaaaccaa cggcgatatc    1320
tccatcaata acgagaaggc ggcagctgca atcgaaaccg ccaaaggctg gtcggcacc    1380 atcgcaccgc agggcgttct cgcttacaag gaagaggaag cacgcggtgt ctggcagacc    1440
ggcaattccg tcttcatgcg caactggccc tatgcctatg cgcttggaaa tggtgccgac    1500
agcgcgatca aggacaagtt cggcgtcacg ccgctgccgg caggtgaaga aggcgcagcc    1560
cccgcttcca cactcggcgg ctggaaccct gctgtttcga atattccga cgatcaggaa    1620 gcggctatcc agctggtaaa attcctggca tcaaaggata cccagaagct gcgcgcgatc    1680
cagctgtcca acatgccgac gatcgcttcg ctttacgacg acaaggatgt cgcggccgca    1740
cagcccttca tgccgacgtg gaagccgatc ttcgagaccg ccgttccgcg tccttccgcc    1800
tcggccaagg tgaaatataa cgaggtttcg gccaagttct ggggcgccgt gcacaacacg    1860
ctctccggca atggtacggc ggcggaaaat ctcgaacttc tcgaggttga actgaccgat    1920
ctcaaaggca acggctgggg cgccggtacc ggtggaatgg tgagcaaggg cgaggagctg    1980
ttcaccgggg tggtgcccat cctggtcgag ctggacggcg acgtaaacgg ccacaagttc    2040
agcgtgtccg gcgagggcga gggcgatgcc acctacggca agctgaccct gaagttcatc    2100
tgcaccaccg gcaagctgcc cgtgccctgg cccaccctcg tgaccacctt cggctacggc    2160
ctgcagtgct tcgcccgcta ccccgaccac atgaagcagc acgacttctt caagtccgcc    2220
atgcccgaag gctacgtcca ggagcgcacc atcttcttca aggacgacgg caactacaag    2280
acccgcgccg aggtgaagtt cgagggcgac accctggtga accgcatcga gctgaagggc    2340
atcgacttca aggaggacgg caacatcctg gggcacaagc tggagtacaa ctacaacagc    2400
cacaacgtct atatcatggc cgacaagcag aagaacggca tcaaggtgaa cttcaagatc    2460
cgccacaaca tcgaggacgg cagcgtgcag ctcgccgacc actaccagca gaacacccc    2520 atcggcgacg gccccgtgct gctgcccgac aaccactacc tgagctacca gtccgccctg    2580
agcaaagacc ccaacgagaa gcgcgatcac atggtcctgc tggagttcgt gaccgccgcc    2640
gggatcactc tcggcatgga cgagctgtac aagtaa                              2676
```

<210> SEQ ID NO 4
<211> LENGTH: 891
<212> TYPE: PRT
<213> ORGANISM: Artificial Sequence
<220> FEATURE:
<223> OTHER INFORMATION: Protein sequence of sucrose biosensor gene

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Ile Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys Gly
225                 230                 235                 240
Gly Thr Gly Gly Ala Ala Glu Ala Ala Glu Leu Ser Ile Ala Ala Asn
                245                 250                 255
Ser Thr Gly Lys Asn Val Ala Phe Phe Arg Glu Arg Ile Ala Ala Phe
            260                 265                 270
Glu Lys Glu Thr Gly His Lys Val Asn Leu Val Thr Met Pro Ser Ser
        275                 280                 285
Ser Ser Glu Gln Phe Ser Gln Tyr Arg Leu Trp Leu Ala Ala Gly Asn
    290                 295                 300
Lys Asp Val Asp Val Tyr Gln Thr Asp Val Ile Trp Ala Pro Gln Leu
305                 310                 315                 320
Ala Glu Gln Phe Val Asp Leu Thr Ala Thr Lys Asp Val Ile Gly
                325                 330                 335
Asp His Phe Pro Ser Ile Val Ala Ser Gln Thr Val Asp Gly Lys Leu
            340                 345                 350
Val Ala Met Pro Met Phe Thr Asp Ala Pro Ala Leu Phe Tyr Arg Lys
        355                 360                 365
Asp Leu Leu Glu Lys Tyr Gly Lys Gln Pro Pro Lys Thr Trp Lys Glu
    370                 375                 380
Leu Ser Glu Thr Ala Lys Glu Val Gln Asp Lys Glu Arg Ala Ala Gly
385                 390                 395                 400
Gln Lys Asp Leu Trp Gly Phe Val Phe Gln Gly Ser Ala Tyr Glu Gly
                405                 410                 415
Leu Thr Cys Asn Ala Leu Glu Trp Ile Ala Ser Ala Gly Gly Gly His
            420                 425                 430
Ile Val Glu Thr Asn Gly Asp Ile Ser Ile Asn Asn Glu Lys Ala Ala
        435                 440                 445
Ala Ala Ile Glu Thr Ala Lys Gly Trp Val Gly Thr Ile Ala Pro Gln
    450                 455                 460
Gly Val Leu Ala Tyr Lys Glu Glu Ala Arg Gly Val Trp Gln Thr
465                 470                 475                 480
Gly Asn Ser Val Phe Met Arg Asn Trp Pro Tyr Ala Tyr Ala Leu Gly
                485                 490                 495
```

```
Asn Gly Ala Asp Ser Ala Ile Lys Asp Lys Phe Gly Val Thr Pro Leu
                500                 505                 510

Pro Ala Gly Glu Gly Ala Ala Pro Ala Ser Thr Leu Gly Gly Trp
        515                 520                 525

Asn Leu Ala Val Ser Lys Tyr Ser Asp Asp Gln Glu Ala Ala Ile Gln
530                 535                 540

Leu Val Lys Phe Leu Ala Ser Lys Asp Thr Gln Lys Leu Arg Ala Ile
545                 550                 555                 560

Gln Leu Ser Asn Met Pro Thr Ile Ala Ser Leu Tyr Asp Asp Lys Asp
                565                 570                 575

Val Ala Ala Ala Gln Pro Phe Met Pro Thr Trp Lys Pro Ile Phe Glu
                580                 585                 590

Thr Ala Val Pro Arg Pro Ser Ala Ser Ala Lys Val Lys Tyr Asn Glu
                595                 600                 605

Val Ser Ala Lys Phe Trp Gly Ala Val His Asn Thr Leu Ser Gly Asn
                610                 615                 620

Gly Thr Ala Ala Glu Asn Leu Glu Leu Leu Glu Val Glu Leu Thr Asp
625                 630                 635                 640

Leu Lys Gly Asn Gly Trp Gly Ala Gly Thr Gly Gly Met Val Ser Lys
                645                 650                 655

Gly Glu Glu Leu Phe Thr Gly Val Val Pro Ile Leu Val Glu Leu Asp
                660                 665                 670

Gly Asp Val Asn Gly His Lys Phe Ser Val Ser Gly Glu Gly Glu Gly
                675                 680                 685

Asp Ala Thr Tyr Gly Lys Leu Thr Leu Lys Phe Ile Cys Thr Thr Gly
690                 695                 700

Lys Leu Pro Val Pro Trp Pro Thr Leu Val Thr Thr Phe Gly Tyr Gly
705                 710                 715                 720

Leu Gln Cys Phe Ala Arg Tyr Pro Asp His Met Lys Gln His Asp Phe
                725                 730                 735

Phe Lys Ser Ala Met Pro Glu Gly Tyr Val Gln Glu Arg Thr Ile Phe
                740                 745                 750

Phe Lys Asp Asp Gly Asn Tyr Lys Thr Arg Ala Glu Val Lys Phe Glu
                755                 760                 765

Gly Asp Thr Leu Val Asn Arg Ile Glu Leu Lys Gly Ile Asp Phe Lys
770                 775                 780

Glu Asp Gly Asn Ile Leu Gly His Lys Leu Glu Tyr Asn Tyr Asn Ser
785                 790                 795                 800

His Asn Val Tyr Ile Met Ala Asp Lys Gln Lys Asn Gly Ile Lys Val
                805                 810                 815

Asn Phe Lys Ile Arg His Asn Ile Glu Asp Gly Ser Val Gln Leu Ala
                820                 825                 830

Asp His Tyr Gln Gln Asn Thr Pro Ile Gly Asp Gly Pro Val Leu Leu
                835                 840                 845

Pro Asp Asn His Tyr Leu Ser Tyr Gln Ser Ala Leu Ser Lys Asp Pro
850                 855                 860

Asn Glu Lys Arg Asp His Met Val Leu Leu Glu Phe Val Thr Ala Ala
865                 870                 875                 880

Gly Ile Thr Leu Gly Met Asp Glu Leu Tyr Lys
                885                 890
```